(12) United States Patent
Hozumi (10) Patent No.: US 7,932,381 B2
(45) Date of Patent: Apr. 26, 2011

(54) PROCESS FOR PRODUCING CARBAPENEM DERIVATIVE AND INTERMEDIATE CRYSTAL THEREFOR

(75) Inventor: Yasuyuki Hozumi, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 820 days.

(21) Appl. No.: 11/884,195

(22) PCT Filed: Feb. 14, 2006

(86) PCT No.: PCT/JP2006/302482
§ 371 (c)(1),
(2), (4) Date: Aug. 13, 2007

(87) PCT Pub. No.: WO2006/087996
PCT Pub. Date: Aug. 24, 2006

(65) Prior Publication Data
US 2008/0171864 A1    Jul. 17, 2008

(30) Foreign Application Priority Data

Feb. 15, 2005 (JP) ................................. 2005-037088
Jul. 1, 2005 (JP) ................................. 2005-193257

(51) Int. Cl.
C07D 477/20 (2006.01)
C07D 207/12 (2006.01)
(52) U.S. Cl. ........................................ 540/350; 548/556
(58) Field of Classification Search .................. 540/350
See application file for complete search history.

(56) References Cited

U.S. PATENT DOCUMENTS

| 5,317,016 A | 5/1994 | Nishitani et al. |
| 5,539,102 A | 7/1996 | Sendo et al. |
| 5,703,243 A | 12/1997 | Nishitani et al. |
| 2006/0229285 A1 | 10/2006 | Uenaka |

FOREIGN PATENT DOCUMENTS

| JP | 64-79180 | 3/1989 |
| JP | 2-15080 | 1/1990 |
| JP | 2003-26680 | 1/2003 |
| JP | 2008303143 A * | 12/2008 |
| WO | 2006/117763 | 11/2006 |

OTHER PUBLICATIONS

International Search Report issued Apr. 25, 2006 in International (PCT) Application No. PCT/JP2006/302482.

Form PCT/IB/338 and International Preliminary Report on Patentability including translation of PCT Written Opinion dated Aug. 30, 2007 issued in International (PCT) Application No. PCT/JP2006/302482.

Yutaka Nishino et al., "Practical Large-Scale Synthesis of Doripenem: A Novel 1 β-Methylcarbapenem Antibiotic", Organic Process Research and Development, vol. 7, No. 6, pp. 846-850, 2003.

* cited by examiner

Primary Examiner — Mark L Berch
(74) Attorney, Agent, or Firm — Wenderoth, Lind & Ponack, L.L.P.

(57) ABSTRACT

An object of the present invention is to provide a carbapenem synthetic intermediate which is advantageous in an industrial process. There are provided a process for producing Compound (I), or a pharmaceutically acceptable salt, or a solvate, or a crystal thereof, comprising reacting Compound (III) and Compound (IV) in the presence of the secondary amine, and a benzyl alcoholated crystal of Compound (I). There are further provided a method of deprotecting Compound (I) with a Pd catalyst, and a crystal of Compound (IV).

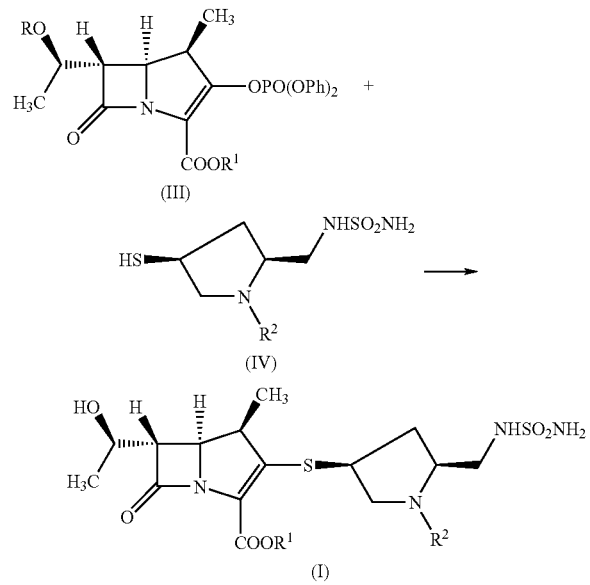

2 Claims, 4 Drawing Sheets

| ピーク番号 | 2θ | 半価幅 | d値 | 強度 | 相対強度 | ピーク番号 | 2θ | 半価幅 | d値 | 強度 | 相対強度 |
|---|---|---|---|---|---|---|---|---|---|---|---|
| 1 | 6.480 | 0.106 | 13.6284 | 193 | 8 | 16 | 19.900 | 0.259 | 4.4578 | 1750 | 65 |
| 2 | 6.840 | 0.106 | 12.9119 | 270 | 11 | 17 | 20.430 | 0.224 | 4.3433 | 523 | 20 |
| 3 | 7.540 | 0.176 | 11.7146 | 2693 | 100 | 18 | 21.280 | 0.168 | 4.1717 | 2083 | 78 |
| 4 | 10.780 | 0.224 | 8.1998 | 453 | 17 | 19 | 21.910 | 0.212 | 4.0532 | 537 | 20 |
| 5 | 11.170 | 0.200 | 7.9145 | 273 | 11 | 20 | 22.850 | 0.118 | 3.8885 | 310 | 12 |
| 6 | 12.900 | 0.141 | 6.9100 | 333 | 13 | 21 | 23.440 | 0.153 | 3.7918 | 743 | 28 |
| 7 | 13.450 | 0.141 | 8.5775 | 223 | 9 | 22 | 23.840 | 0.176 | 3.7292 | 1050 | 39 |
| 8 | 14.090 | 0.271 | 6.2802 | 247 | 10 | 23 | 24.310 | 0.153 | 3.6582 | 540 | 21 |
| 9 | 14.970 | 0.118 | 5.9128 | 263 | 10 | 24 | 25.320 | 0.247 | 3.5145 | 680 | 26 |
| 10 | 15.740 | 0.212 | 5.6253 | 567 | 22 | 25 | 25.630 | 0.176 | 3.4727 | 733 | 28 |
| 11 | 16.040 | 0.141 | 5.5208 | 260 | 10 | 26 | 26.660 | 0.212 | 3.3408 | 500 | 19 |
| 12 | 17.650 | 0.224 | 5.0207 | 1043 | 39 | 27 | 27.230 | 0.212 | 3.2722 | 417 | 16 |
| 13 | 18.470 | 0.247 | 4.7996 | 1237 | 46 | 28 | 28.180 | 0.176 | 3.1640 | 493 | 19 |
| 14 | 19.190 | 0.118 | 4.6211 | 423 | 16 | 29 | 28.730 | 0.259 | 3.1046 | 707 | 27 |
| 15 | 19.500 | 0.198 | 4.5463 | 813 | 33 | 30 | 29.510 | 0.106 | 3.0243 | 290 | 11 |

| ピーク番号 | 2θ | 半価幅 | d値 | 強度 | 相対強度 | ピーク番号 | 2θ | 半価幅 | d値 | 強度 | 相対強度 |
|---|---|---|---|---|---|---|---|---|---|---|---|
| 31 | 30.000 | 0.153 | 2.9780 | 343 | 13 | 46 | 38.770 | 0.141 | 2.3206 | 397 | 15 |
| 32 | 30.340 | 0.106 | 2.8869 | 337 | 13 | 47 | 39.400 | 0.106 | 2.2850 | 480 | 18 |
| 33 | 31.560 | 0.176 | 2.8324 | 477 | 18 | 48 | 39.570 | 0.118 | 2.2756 | 353 | 14 |
| 34 | 32.160 | 0.141 | 2.7809 | 463 | 18 | | | | | | |
| 35 | 32.980 | 0.200 | 2.7152 | 423 | 16 | | | | | | |
| 36 | 33.740 | 0.224 | 2.6542 | 513 | 20 | | | | | | |
| 37 | 35.100 | 0.118 | 2.5544 | 313 | 12 | | | | | | |
| 38 | 35.620 | 0.129 | 2.5183 | 490 | 19 | | | | | | |
| 39 | 35.740 | 0.153 | 2.5101 | 517 | 20 | | | | | | |
| 40 | 36.810 | 0.153 | 2.4396 | 460 | 18 | | | | | | |
| 41 | 37.200 | 0.118 | 2.4149 | 453 | 17 | | | | | | |
| 42 | 37.340 | 0.106 | 2.4082 | 397 | 15 | | | | | | |
| 43 | 37.880 | 0.129 | 2.3731 | 343 | 13 | | | | | | |
| 44 | 38.100 | 0.106 | 2.3588 | 340 | 13 | | | | | | |
| 45 | 38.250 | 0.200 | 2.3510 | 367 | 14 | | | | | | |

PROCESS FOR PRODUCING CARBAPENEM DERIVATIVE AND INTERMEDIATE CRYSTAL THEREFOR

TECHNICAL FIELD

The present invention relates to a process for producing a carbapenem derivative and an intermediate crystal therefor.

BACKGROUND TECHNIQUE

A pyrrolidylthiocarbapenem derivative (Compound (II)) having a broad range of an antibacterial spectrum is known as a useful antibiotic (see: Patent Literature 1). Compound (I) of the present invention is a synthetic intermediate therefor.

[Chemical formula 1]

(wherein $R^1$ is a carboxy protecting group: $R^2$ is an amino protecting group)

As an example of production of Compound (I), Patent Literature 1 (Example 13, step 3) describes the following method, but a base used at a condensation reaction for introducing a 2-positional side chain is diisopropylethylamine (yield 71%).

[Chemical formula 2]

(I-a)

In addition, Patent Literature 2 (Reference Example 1) also describes the following similar reaction, but a base used at a condensation reaction is the same diisopropylethylamine (yield 54%).

[Chemical formula 3]

Further, a method of synthesizing a carbapenem derivative having a pyrrolidinylthio group of another structure at a 2-position is known, but as a base at a condensation reaction at a 2-position, diisopropylethylamine is also used (see: Patent Literature 3, Examples 1, 7 etc.).

Like this, as the base at a 2-positional condensation reaction of carbapenem, tertiary amine such as diisopropylethylamine and the like is generally used. The reason is presumed as follows: tertiary amine is generally strongly basic, and it is thought that a side reaction hardly occurs because there is not hydrogen on the N atom.

In addition, regarding crystallization of the Compound (I-a), various alcoholated crystals (example: 2-propanol, 2-pentanol, 1-pentanol, t-amyl alcohol, 1-propanol) are known (see: Patent Literature 2).

In addition, the Compound (IV-a) which is a synthetic intermediate for Compound (I-a) is described in Patent Literature 1 (see: Preparation Example 8), but a crystal thereof is not isolated.

Further, as a method of deprotecting Compound (I-a), a Sn reagent (see: Patent Literature 1) and Meldrum's acid (see: Patent Literature 2) were used, but from a viewpoint of loading on the environment and stability of a reagent itself, they were not preferable for industrial implementation. On the other hand, as other reagent for deprotecting a carbapenem derivative, a combination of amine and a Pd catalyst is known (see: Patent Literature 4). In Patent Literature 4, amine is used as a receptor for a lower alkenyl group, and as preferable amine, there is exemplified aromatic amines such as aniline, N-methylaniline and the like.

[Patent Literature 1]
Japanese Patent Application Laid-Open (JP-A) No. 05-294970
[Patent Literature 2]
WO/2004/72073
[Patent Literature 3]
JP-A No. 2-15080
[Patent Literature 4]
JP-A No. 64-79180

DISCLOSURE OF THE INVENTION

Problems to be Solved by the Invention

Development of a further preferable industrial process for producing Compound (I) which is an intermediate of a carbapenem derivative is desired. In addition, development of a further preferable crystal of Compound (I) is desired. Further, development of an industrially preferable method of deprotecting Compound (I), and a crystal of Compound (IV-a) or the like which is an intermediate of Compound (I) is desired.

Means to Solve the Problems

In view of the above problems, the present inventors intensively continued to study and, as a result, found out that, when a particular base, preferably secondary amine is used at a 2-positional condensation reaction of carbapenem, a reaction yield is improved, a reaction time is shortened, and Compound (I) can be effectively produced. In addition, it was also found out that, when Compound (I) is crystallized from benzyl alcohol or the like, a crystal which is excellent in handling as an intermediate is obtained. Further, a method of deprotecting Compound (I) in the presence of a Pd catalyst and particular amine, and a crystal of Compound (IV-a) or the like were found out, resulting in completion of the following present invention.

(1) A process for producing Compound (I) represented by the formula:

[Chemical formula 6]

(I)

(wherein $R^1$ and $R^2$ are as defined below), or a pharmaceutically acceptable salt thereof, or a solvate or a crystal thereof, comprising:

reacting Compound (III) represented by the formula:

[Chemical formula 4]

(III)

(wherein R is hydrogen or a hydroxyl protecting group; $R^1$ is a carboxy protecting group; Ph is phenyl)

with Compound (IV) represented by the formula:

[Chemical formula 5]

(IV)

(wherein $R^2$ is an amino protecting group), or a pharmaceutically acceptable salt thereof in the presence of secondary amine and, optionally, deprotecting the hydroxyl protecting group.

(2) The process according to (1), wherein the secondary amine is diisopropylamine.

(3) The process according to (1) or (2), wherein $R^1$ is $CH_2CH=CH_2$; $R^2$ is $COOCH_2CH=CH_2$.

(4) A process for producing Compound (II) represented by the formula:

[Chemical formula 7]

(II)

or a pharmaceutically acceptable salt thereof, or a solvate thereof, comprising:

obtaining Compound (I), or a pharmaceutically acceptable salt thereof, or a solvate or a crystal thereof by a method as defined in any one of (1) to (3), and subjecting this to a deprotecting reaction.

(5) A solvated crystal (provided that the solvent is optionally substituted benzyl alcohol) of Compound (I-a) represented by the formula:

[Chemical formula 8]

(I-a)

(6) The crystal according to (5), which is a benzyl alcoholated crystal.
(7) The crystal according to (3), wherein a content of benzyl alcohol is 1 to 10 mole equivalent relative to Compound (I).
(8) The crystal according to (6) or (7), wherein a main peak is present at a diffraction angle 2θ=around 7.6, 17.7, 18.5, 19.5, 19.9, 21.3, 23.8 (unit:degree) in a powder X-ray diffraction pattern.
(9) A process for producing Compound (II) represented by the formula:

[Chemical formula 9]

(II)

or a pharmaceutically acceptable salt thereof, or a solvate thereof, comprising:
deprotecting a crystal as defined in any one of (5) to (8).
(10) The process for producing Compound (II), or a pharmaceutically acceptable salt thereof, or a solvate thereof according to (9), comprising obtaining Compound (I), or a pharmaceutically acceptable salt thereof, or a solvate thereof by the method as defined in any one of (1) to (3), crystallizing this in optionally substituted benzyl alcohol to obtain an optionally substituted benzyl alcoholated crystal of Compound (I), and deprotecting this.
(11) A process for producing Compound (II) represented by the formula:

[Chemical formula 16]

(II)

or a pharmaceutically acceptable salt thereof, or a solvate thereof, comprising:

deprotecting a compound represented by the formula:

[Chemical formula 15]

(I)

(wherein $R^1$ is a carboxy protecting group; $R^2$ is an amino protecting group),
or a solvate thereof or a crystal thereof in the presence of a Pd catalyst and N-ethylaniline.
(12) The process according to (11), wherein $R^1$ is $CH_2CH=CH_2$; $R^2$ is $COOCH_2CH=CH_2$.
(13) The process according to (11), wherein an amount of the Pd catalyst to be used is 0.01 mole equivalent or less relative to Compound (I).
(14) The process according to (11), wherein an amount of the Pd catalyst to be used is 0.005 mole equivalent or less relative to Compound (I).
(15) A crystal of a compound represented by the formula:

[Chemical formula 17]

(IV-a)

(16) The crystal according to (15), wherein a main peak is present at a diffraction angle 2θ=around 6.26, 12.50, 18.24, 18.80, 23.90, and 26.86 (unit:degree) in a powder X-ray diffraction pattern.
(17) A crystal of a compound represented by the formula:

[Chemical formula 18]

(V-a)

(wherein Ac is acetyl; Boc is t-butoxycarbonyl).
(18) The crystal according to (17), wherein a main peak is present at a diffraction angle 2θ=around 10.24, 12.26, 13.34, 17.32, 20.84, 21.22, 21.72 and 22.28 (unit:degree) in a powder X-ray diffraction pattern.

Effect of the Invention

According to the present process, Compound (I) can be produced at a better yield and in a short time. In addition, a solvated crystal of Compound (I) which is excellent in handling is obtained. In addition, a method of deprotecting Compound (I) in the presence of a Pd catalyst, and a crystal of an intermediate are provided. By utilizing these processes, and crystals, Compound (II) which is a carbapenem antibacterial agent, or a solvate thereof, or a crystal thereof can be effectively produced.

BEST MODE FOR CARRYING OUR THE INVENTION (1) Production of Compound (I)

[Chemical formula 10]

(wherein R is hydrogen or a hydroxy protecting group; $R^1$ is a carboxy protecting group; $R^2$ is an amino protecting group, and Ph is phenyl)

By reacting Compound (III) with Compound (IV) or a pharmaceutically acceptable salt thereof in the presence of a base and, optionally, deprotecting the hydroxy protecting group, Compound (I), or a pharmaceutically acceptable salt thereof, or a solvate thereof or a crystal thereof is obtained.

As the base, secondary amine is used, and more preferable is secondary amine having relatively great steric hindrance. Specifically, it is represented by $NHR^aR^b$, wherein $R^a$ and $R^b$ are independently alkyl, phenyl or the like, preferably $R^a$ and $R^b$ are the same. The alkyl is straight or branched C1-C10, preferably C3-C7alkyl, more preferably is branched. As $R^a$ and $R^b$, isopropyl, t-butyl, isobutyl, amyl and phenyl are further preferably exemplified. As secondary amine, more preferable are diisopropylamine, di-t-butylamine, diisobutylamine, diamylamine, and diphenylamine, particularly preferable is dialkylamine (e.g.: diisopropylamine).

Examples of a reaction solvent include acetonitrile, dimethylformamide, methylene chloride, dimethyl sulfoxide, N-dimethylacetamide and the like, preferably N-dimethylacetamide.

A reaction temperature is usually −40° C. to room temperature, preferable about −20 to 0° C.

A reaction time is usually a few tens minutes to a few tens hours, preferably 1 to 5 hours.

Compound (III) and Compound (IV) are used at an amount of 10:1 to 1:10, preferably 1:1 to 1:5.

Examples of the pharmaceutically acceptable salt include inorganic base salts (e.g.: alkali metal salts such as sodium salt, potassium salt etc.; alkaline earth metal salts such as calcium salt, magnesium salt etc.; ammonium salt); organic base salts (e.g.: triethylamine salt, pyridine salt, picoline salt, ethanolamine salt, triethanolamine salt, dicyclohexylamine salt, N,N'-dibenzylethylenediamine salt); inorganic acid addition salts such as hydrochloride, hydrobromide, sulfate, phosphate etc.; organic acid addition salts such as formate, acetate, trifluoroacetate, maleate, tartrate, methanesulfonate, benzenesulfonate etc.; salts with basic amino acids or acidic amino acids such as arginine, aspartic acid, glutamic acid etc.

As the hydroxy protecting group represented by R, various hydroxyl protecting groups which can be generally used in the field of β-lactam antibacterial agents can be used. Specific examples include trialkylsilyl (the alkyl is preferably C1-C6, e.g.: trimethylsilyl, triethylsilyl, t-butyldimethylsilyl, triisopropylsilyl, dimethylhexylsilyl, t-butyldiphenylsilyl), optionally substituted benzyl (example of substituent: nitro, lower alkoxy), lower alkoxycarbonyl group (e.g.: methoxycarbonyl, ethoxycarbonyl), halogeno lower alkoxycarbonyl group, optionally substituted benzyloxycarbonyl (example of substituent: nitro, lower alkoxy), acyl (e.g.: acetyl, benzoyl), aralkyl (e.g.: triphenylmethyl), tetrahydropyranyl and the like. Preferable is trialkylsilyl, particularly preferable is trimethylsilyl and t-butyldimethylsilyl.

These hydroxy protecting groups can be optionally deprotected by methods well-known to a person skilled in the art after a reaction. Alternatively, those protecting groups may be protecting groups which are automatically eliminated during a coupling reaction or at a post-treatment (e.g.: extraction, washing) step. For example, trimethylsilyl or the like is eliminated with an acid in an extraction procedure after a reaction.

Examples of the carboxy protecting group represented by $R^1$ include lower alkyl (e.g.: methyl, ethyl, propyl, isopropyl, butyl, isobutyl, tertiary butyl, pentyl, hexyl), lower alkanoyloxy (lower)alkyl (e.g.: acetoxymethyl, propionyloxymethyl, butyryloxymethyl, valeryloxymethyl, pivaloyloxymethyl, hexanoyloxymethyl), lower alkanesulfonyloxy (lower)alkyl (e.g.: 2-mesylethyl), mono (or di or tri) halo (lower)alkyl (e.g.: 2-iodoethyl, 2,2,2-trichloroethyl), lower alkoxycarbonyloxy (lower)alkyl (e.g.: methoxycarbonyloxymethyl, ethoxycarbonyloxymethyl, propoxycarbonyloxymethyl, tertiary butoxycarbonyloxymethyl, 1- (or 2-)methoxycarbonyloxyethyl, 1- (or 2-)ethoxycarbonyloxyethyl, 1- (or 2-)isopropoxycarbonyloxyethyl), lower alkenyl (e.g.: vinyl, allyl), lower alkynyl (e.g.: ethynyl, propynyl), (substituted) aryl (lower)alkyl (e.g.: benzyl, 4-methoxybenzyl, 4-nitrobenzyl, phenethyl, trityl, benzhydryl, bis(methoxyphenyl)methyl, 3,4-dimethoxybenzyl, 4-hydroxy-3,5-di-tertiary butylbenzyl), (substituted) aryl (e.g.: phenyl, 4-chlorophenyl, tolyl, tertiary butylphenyl, xylyl). Among them, $R^1$ is preferably lower alkyl, lower alkenyl (e.g.: vinyl, allyl), lower alkynyl, (substituted) aryl(lower)alkyl, or (substituted) aryl since there is a great advantage of utilization of the present process in the case of a relatively electron donating protecting group. Further preferable is a protecting group which is hardly eliminated during a coupling reaction, and particularly preferable is allyl (—CH$_2$CH=CH$_2$).

Examples of the amino protecting group represented by $R^2$ include aliphatic acyl groups derived from carboxylic acid, carbonic acid, sulfonic acid and carbamic acid, and aliphatic acyl groups substituted with an aromatic group.

Examples of the aliphatic acyl group include saturated or unsaturated alicyclic or cyclic acyl groups, for example, alkanoyl groups such as lower alkanoyl groups such as formyl, acetyl, propionyl, butyryl, isobutyryl, valeryl, isovaleryl, pivaloyl, hexanoyl and the like, alkylsulfonyl groups such as lower alkylsulfonyl groups such as mesyl, ethylsulfonyl, propylsulfonyl, isopropylsulfonyl, butylsulfonyl, isobutylsulfonyl, pentylsulfonyl, hexylsulfonyl and the like, carbamoyl groups, for example, N-alkylcarbamoyl groups such as methylcarbamoyl, ethylcarbamoyl and the like, alkoxycarbonyl groups such as lower alkoxycarbonyl groups such as methoxycarbonyl, ethoxycarbonyl, propoxycarbonyl, butoxycarbonyl, tertiary butoxycarbonyl and the like, alkenyloxycarbonyl groups such as lower alkenyloxycarbonyl groups such as vinyloxycarbonyl, allyloxycarbonyl and the like, alkenoyl groups such as lower alkenoyl groups such as acryloyl, methacryloyl, crotonoyl and the like, and cycloalkanecarbonyl groups such as cyclo(lower)alkanecarbonyl groups such as cyclopropanecarbonyl, cyclopentanecarbonyl, cyclohexanecarbonyl and the like.

Examples of the aliphatic acyl group substituted with an aromatic group include aralkoxycabonyl groups such as phenyl(lower)alkoxycarbonyl groups such as benzyloxycarbonyl, phenethyloxycarbonyl and the like.

These acyl groups may be further substituted with one or more suitable substituents such as a nitro group, and examples of such the preferable acyl group having a substituent include nitroaralkoxycarbonyl groups such as nitrobenzyloxycarbonyl and the like.

The amino protecting group is preferably a protecting group which is hardly eliminated during a coupling reaction, particularly preferably an alkenyloxycarbonyl group (e.g.: —COOCH$_2$CH=CH$_2$).

(2) Crystal of Compound (I-a)

Compound (I-a) can be crystallized from an alcohol solvent. The alcohol is preferably optionally substituted benzyl alcohol, and the alcoholated crystal is obtained. Examples of a substituent of optionally substituted benzyl alcohol include lower alkyl, preferably C1-C4 alkyl (e.g.: methyl, ethyl, propyl), lower alkoxy (e.g.: methoxy, ethoxy, propoxy), halogen (e.g.: F, Cl, Br), optionally substituted amino (example of substituent: lower alkyl), nitro, cyano, OH and the like, and a substitution position may be any of ortho, meta and para.

The optionally substituted benzyl alcoholated crystal is preferably a benzyl alcoholated crystal. A content of benzyl alcohol in the benzyl alcoholated crystal is 0.1 to 5 mole equivalent, preferably 0.5 to 2 mole equivalent, more preferably 1 mole equivalent relative to Compound (I-a). The benzyl alcoholated crystal preferably exhibits a pattern of FIG. 1 in powder X-ray diffraction.

The benzyl alcoholated crystal preferably has a main peak around on at least following positions indicated below in a powder X-ray diffraction pattern.

2θ=7.6, 17.7, 18.5, 19.5, 19.9, 21.3, 23.8 (unit:degree) (X-ray diffraction measuring condition: tubular lamp CuKα ray, tubular voltage 30 Kv, tubular current 15 mA, dsin θ=nλ (n is integer, θ is diffraction angle))

The aforementioned spacing d value is such that, among X-ray peaks, main peaks having a strong relative intensity are selected, but a crystal structure is not particularly limited only by these values. That is, peaks other than these peaks may be contained. In addition, generally, when a crystal is measured by X-ray analysis, peaks may generate a slight measurement error, depending on a measuring instrument, measuring condition, the presence of an attached solvent or the like. For example, a measurement error of around ±0.2 as expressed by a value of spacing d may be generated in some cases and, even when a very precise facility is used, a measurement error of around ±0.01 to ±0.1 may be generated in some cases. Therefore, upon identification of a crystal structure, slight error may be taken into consideration, and all of crystals which are characterized by substantially the same X-ray pattern as that described above are within the scope of the present invention.

When the benzyl alcoholated crystal is prepared from Compound (I-a), preferably, the compound is obtained by dissolving Compound (I-a) or a solvate thereof in a soluble solvent, adding benzyl alcohol, stirring this at room temperature for a few hours and, optionally allowing to stand this at 0° C. to room temperature for a few hours to a few days, followed by filtering and drying according to a conventional method. Alternatively, after Compound (I-a) or a solvate thereof is dissolved in a large amount of a solvent, a solvent is once distilled off to obtain a concentrate, to this are added benzyl alcohol and, optionally, other organic solvent, and stirring, filtration, drying and the like may be performed as described above.

As the solvent, following soluble solvents, insoluble solvents and a mixture thereof are exemplified.

As the soluble solvent, alcohols such as methanol, ethanol, ethylene glycol, methoxyethanol, glycerin, and propylene glycol, ethers such as dioxane, tetrahydrofuran, and dimethoxyethane, ketones such as acetone, methyl ethyl ketone, and methyl isobutyl ketone, esters such as methyl formate, ethyl formate, propyl formate, methyl acetate, ethyl acetate, propyl acetate, butyl acetate, methyl propionate, and ethyl propionate, organic halogenated hydrocarbons such as dichloromethane, chloroform, carbon tetrachloride, 1,2-dichloroethane, trichloroethane, chlorobenzene, dichlorobenzene, nitriles such as acetonitrile, and propionitrile, dimethylformamide, dimethyl sulfoxide, N-methylpyrrolidone, quinoline, pyridines, and triethylamine can be used. These solvents may be used alone, or two or more kinds may be used by mixing them. Alternatively, they may be used by mixing with water. Preferable is ethyl acetate.

As the insoluble solvent, alcohols such as 2-propanol, 2-pentanol, 1-pentanol, t-amyl alcohol, 1-propanol, n-propanol, t-propanol, isobutanol, n-butanol, cyclohexanol, and benzyl alcohol, ethers such as diethyl ether, isopropyl ether, dibutyl ether, ethyl isoamyl ether, and ethyl phenyl ether, and hydrocarbons such as n-pentane, n-hexane, n-heptane, n-octane, n-decane, cyclohexane, methylcyclohexane, toluene, benzene, ethylbenzene, cumene, cymene, and xylene can be used. These solvents may be used alone, or two or more kinds may be used by mixing them.

A ratio of the soluble solvent and the insoluble solvent to be used is usually 1:0 to 1:1000, preferably 1:0.1 to 1:100, particularly preferably 1:1 to 1:50, or usually 0:1 to 1000:1, preferably 0.1:1 to 100:1, particularly preferably 1:1 to 50:1 by weight. Preferably, ethyl acetate and benzyl alcohol are used at a ratio of 1:1 to 5.

A benzyl alcoholated crystal of Compound (I-a) has excellent crystallizability as apparent from its clear X-ray peaks. Therefore, when Compound (I-a) is synthesized by a 2-positional condensation reaction, and is isolated as a benzyl alcoholated crystal, an objective substance is obtained at a better yield and a high purity. In addition, handling property is better, and storage stability is high. Therefore, this is very useful as a synthetic intermediate for Compound (II) which is a carbapenem antibacterial agent. Alternatively, when Compound (I-a) is isolated as a benzyl alcoholated crystal from a reaction solution after a 2-positional condensation reaction, preferably, the compound may be crystallized by washing the reaction extract, distilling a solvent off, drying this, dissolving the material in a soluble solvent as described above, and adding benzyl alcohol and, optionally, other insoluble solvent. Alternatively, in adding benzyl alcohol, optionally, a separately prepared benzyl alcoholated crystal of Compound (I-a) may be added as a seed crystal.

(3) Step of Deprotecting Compound (I), or a Solvate or a Crystal Thereof

By subjecting Compound (I), a pharmaceutically acceptable salt thereof, or a solvate or a crystal thereof, preferably a benzyl alcoholated crystal of Compound (I-a) to a deprotecting reaction, Compound (II) which is an antibacterial agent disclosed in JP-A No. 05-294970, or a pharmaceutically acceptably salt, or a solvate thereof, or a crystal thereof is obtained.

The deprotecting reaction is performed according to the method well-known to a person skilled in the art. In the present reaction, a nickel catalyst, a cobalt catalyst, an iron catalyst, a copper catalyst and a noble metal catalyst such as a platinum catalyst and a palladium catalyst are used. Preferably, the palladium catalyst and the nickel catalyst are used, and more preferably, tetrakis(triphenylphosphine)palladium, (triphenylphosphine)palladium acetate and (triethylphosphite)palladium acetate are used. An additive (preferably triphenylphosphine etc.) may be added to a mixed solution to which palladium has been added. Further preferably, a reducing agent for reduction-removing a protecting group or a nucleophile (trapping agent for aryl group) is added to the palladium catalyst. The reducing agent is hydrogen, metal hydride or the like, preferably tri-n-butyltin hydride or the like. Examples of the nucleophile include carboxylate (e.g. sodium 2-ethylhexanoate etc.), 1,3-dicarbonyl compound (e.g. Meldrum's acid, dimedone and malonic acid ester etc.), secondary amine (e.g. diethylamine etc.), and aromatic amine.

When the environmental aspect and a reaction yield are taken into consideration, a deprotecting reagent is more preferably a combination of a palladium catalyst (e.g.: tetrakis (triphenylphosphine)palladium) and aromatic amine (e.g.: aniline derivative). Examples of the aniline derivative include aniline, N-methylaniline, N-ethylaniline, N,N-dimethylaniline, and electron donating group-substituted anilines such as o-, m- or p-toluidine, o-, m- or p-anisidine and the like, particularly preferably N-ethylaniline. By using N-ethylaniline, even when an amount of the Pd reagent to be used is considerably reduced (e.g.: not more than 0.01 mole equivalent, preferably not more than 0.005 mole equivalent, more preferably 0.003 to 0.001 mole equivalent relative to Compound (I)), a deprotecting reaction proceeds at a high yield. In addition, a production rate of byproduct which is derived from a protecting group and aniline reagent is low and, further, handling procedure of Compound (II) precipitated after deprotection is better, being suitable as a large scale production method.

An amount of aromatic amine (e.g.: aniline derivative) to be used is 1 to 20 mole equivalent, preferably 5 to 15 mole equivalent relative to Compound (I).

As a solvent used in the deprotecting reaction, any solvent may be used as far as it is used in a normal reaction. Preferable are acetone, acetonitrile, ethyl acetate, dichloromethane, tetrahydrofuran, methanol, ethanol and water. These solvents may be used alone, or two or more kinds may be used by mixing them. Particularly preferable is a combination of tetrahydrofuran and water, and the combination is preferably used at a ratio of tetrahydrofuran: water=1:1 to 10:1.

Compound (I), or a pharmaceutically acceptable salt thereof, or a solvate or a crystal thereof, and a nucleophile are added to a solvent, and a reaction system (e.g. a reaction mixed solution and a vessel) is preferably filled with nitrogen.

A reaction temperature is in a range of about −20 to 50° C., preferably 0 to 30° C.

A reaction time is usually a few minutes to a few tens hours, preferably in a range of 1 to 3 hours.

The present invention further provides each crystal of Compound (IV-a) and (V-a) which are a synthetic intermediate for Compound (I-a).

[Chemical formula 19]

(Ac=acetyl; Boc=t-butoxycarbonyl)

(1) Crystal of Compound (IV-a)

Figure 3:
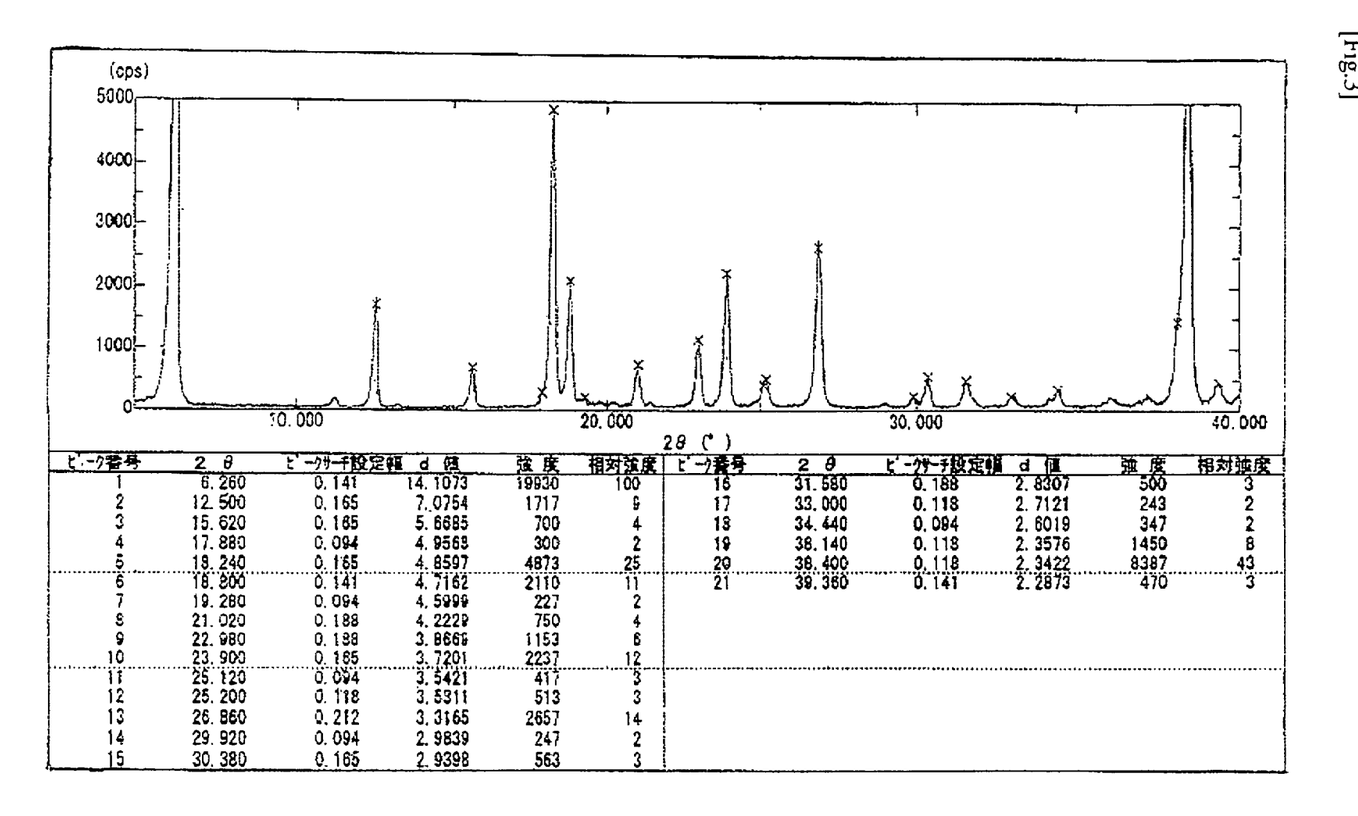
FIG. 3 is a chart of a powder X-ray diffraction pattern of a crystal of Compound (IV-a) obtained in Example 7.

The present crystal has main peaks around diffraction angle 2θ=at least 6.26, 12.50, 18.24, 18.80, 23.90, and 26.86 (unit:degree) in a powder X-ray diffraction pattern. More particularly, a pattern in FIG. 3 is shown. A crystal of Compound (IV-a) may be a solvate (e.g.: hydrate, alcoholate).

(2) Crystal of Compound (V-a)

Figure 4:
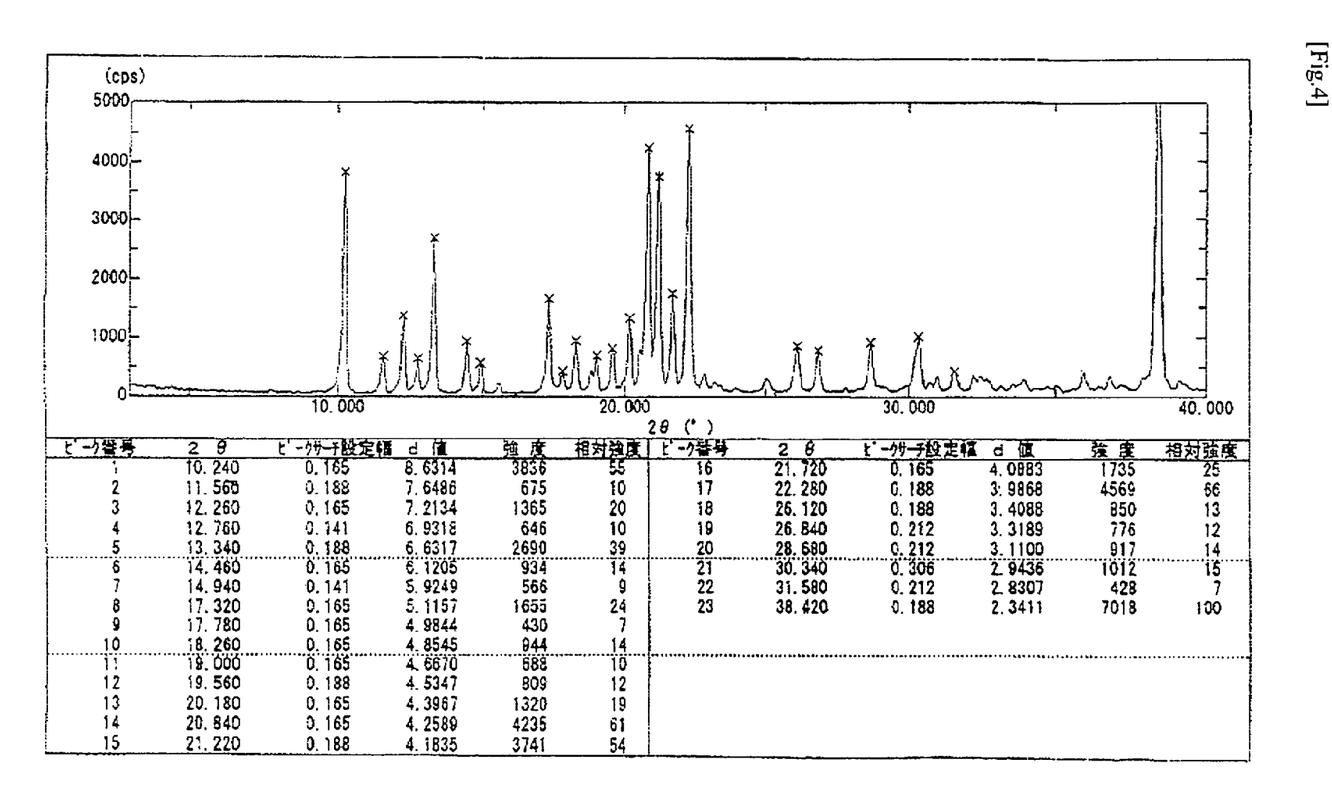
FIG. 4 is a chart of a powder X-ray diffraction pattern of a crystal of Compound (V-a) obtained in Example 7.

The present crystal has main peaks around diffraction angle 2θ=at least 10.24, 12.26, 13.34, 17.32, 20.84, 21.22, 21.72 and 22.28 (unit:degree) in a powder X-ray diffraction pattern. More particularly, a pattern in FIG. 4 is shown. A crystal of Compound (V-a) may be a solvate (e.g.: hydrate, alcoholate).

A crystal of Compound (IV-a), as shown in Example later, can be crystallized with an organic solvent (preferably ethyl acetate-toluene system) after a crystal of Compound (V-a) is deprotected with preferably an acid, more preferably an inorganic acid (e.g.: hydrochloric acid), a pH of the reaction is adjusted with an alkali (preferably pH 2 to 3) to precipitate the compound, and dried and concentrated by a conventional method. Alternatively, after Compound (VI-a) is reacted with H$_2$NSO$_2$NHBoc to produce Compound (V-a), this may be subsequently subjected to a deprotecting reaction without isolation as described above. When there is a possibility that a byproduct derived from an amino-protecting group is generated at a deprotecting reaction, preferably, a radical trapping agent may be used jointly. Examples of the radical trapping agent include dibutylhydroxytoluene.

In the present process, by using the above-obtained Compound (I), a pharmaceutically acceptable salt, a solvate thereof or a crystal thereof, having a high purity, it has become possible to prepare an aqueous solution in which an objective Compound (II) is dissolved at a high concentration, in an impurity extraction procedure using water and an organic solvent, preferably dichlohomethane after a deprotecting reaction. As a result, concentration and column chromatography treatment which have previously been essential in a post-treatment step become not an essential procedure, and it has become possible to easily isolate an objective pyrrolidylthiocarbapenem derivative (II), or a pharmaceutically acceptable salt, or a solvate or a crystal thereof. Therefore, the present process is useful also as an industrial process.

Examples will be shown below.

EXAMPLE 1

[Chemical formula 11]

(I-a)

2-Propanolated crystal (3.340 g, corresponding to 3.137 g in terms of non-solvent) of Compound (I-a) described in WO 2004/72073 was dissolved in ethyl acetate (67 ml), and ethyl acetate and isopropanol were distilled off to obtain an ethyl acetate concentrate (4.551 g). To this were added ethyl acetate (3.14 ml), benzyl alcohol (3.14 ml), and toluene (12.55 ml), and the mixture was stirred at room temperature for 2 hours, and at 5° C. for 1 hour. The precipitated crystal was filtered, washed with toluene (6.26 ml), and air-dried to obtain a benzyl alcoholated crystal of Compound (I-a) (3.668 g, corresponding to 3.037 g in terms of non-solvent, containing benzyl alcohol (1.0 mol)). Yield: 96.8%

Mp. 74.9° C.

Elementary Analysis for $C_{22}H_{31}N_4O_8S_2 \cdot 1.0C_7H_8O \cdot 0.2H_2O$

Calcd: C: 53.15, H: 6.06, N: 8.55, S: 9.79

Found: C: 53.19, H: 6.12, N: 8.65, S: 9.85

Figure 1:
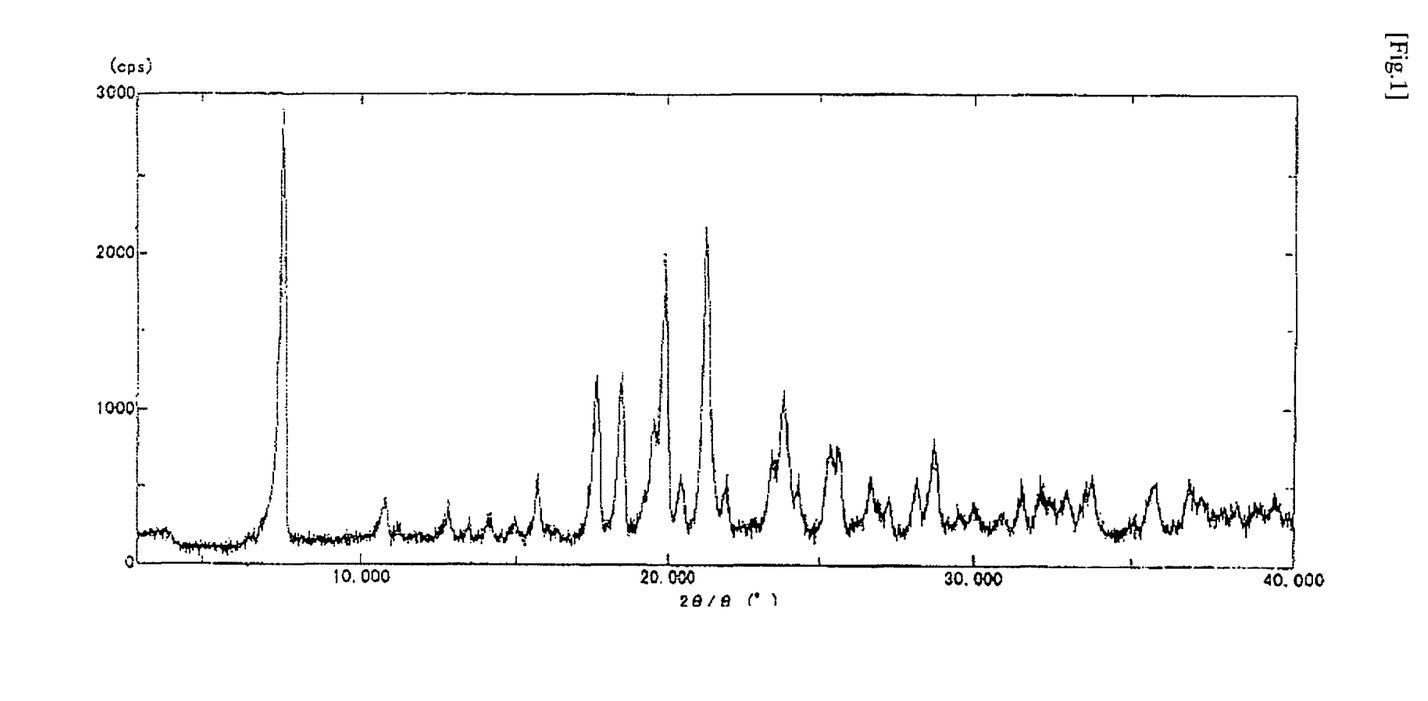
FIG. 1 is a chart of a powder X-ray diffraction pattern of a benzyl alcoholated crystal of Compound (I-a) obtained in Example 1.
Figure 2:
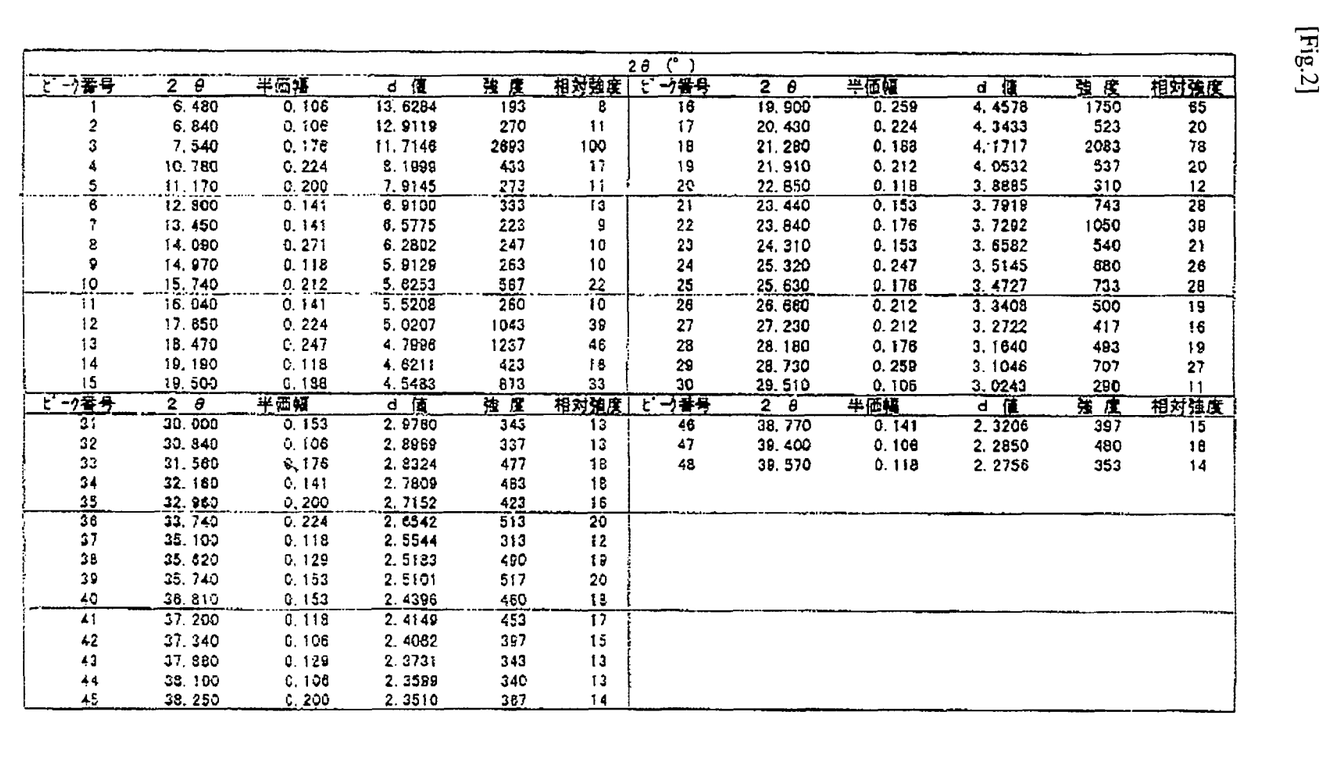
FIG. 2 shows peak values of a powder X-ray diffraction pattern of a benzyl alcoholated crystal of Compound (I-a) obtained in Example 1.

Powder X-ray diffraction: a chart is shown in FIG. 1 and peak values are shown in FIG. 2.

Regarding other alcohol solvate crystals of Compound (I-a) (solvent example: 2-propanol, 2-pentanol, 1-pentanol, t-amyl alcohol, 1-propanol), when stored under the general environment of 25° C. and 1 atom, phenomenon was recognized, in which the crystal was effloresced with time, and an amount of a contained solvent was reduced. However, regarding a benzyl alcoholated crystal, such the phenomenon was not recognized in handling for a few days, and it was seen that the crystal has high stability.

EXAMPLE 2

Amorphous powdery Compound (I-a) (100 mg) was dissolved in ethyl acetate (0.1 ml), benzyl alcohol (0.3 ml) was added, and the mixture was stirred at room temperature for 1 hour, and allowed to stand at 5° C. for 2 days. A precipitated crystal was filtered, and air-dried to obtain a benzyl alcoholated crystal of Compound (I-a) (79 mg) exhibiting substantially the same powder X-ray pattern as that of Example 1.

EXAMPLE 3

[Chemical formula 12]

+

(III-a)

(IV-a)

(I-a)

(wherein Me=methyl; Ph=phenyl)

Diisopropylamine (0.168 ml; 1.2 mmol) was added dropwise to a solution of 595 mg (1 mmol) of enolphosphate (III-a) in which hydroxy on a 6-positional side chain was protected, and 345 mg (1.1 mmol) of thiol (IV-a) in 2 ml of N-dimethylacetamide at −12 to −8° C., and the mixture was stirred at the same temperature for 1 hour and 30 minutes. At this time point, it was confirmed by HPLC that a condensation reaction proceeded 92%. The reaction solution was poured into dilute hydrochloric acid, followed by extraction with ethyl acetate. The organic layer was sequentially washed with water, a 5% aqueous sodium bicarbonate solution, and water, and dried with sodium sulfate, and a solvent was distilled off. The residue was dissolved in 2 ml of ethyl acetate, 0.5 ml of benzyl alcohol, and a crystal obtained in Example 2 as a seed crystal were added, and the mixture was stirred at room temperature for 2 hours. Toluene (5 ml) was slowly added, and the mixture was further stirred at room temperature for 2 hours, and cooled to 5° C. After filtration and drying, 554 mg (85%) of a benzyl alcoholated crystal of Compound (I-a) exhibiting substantially the same powder X-ray pattern as that of Example 1 was obtained.

EXAMPLE 4

[Chemical formula 13]

Diisopropylamine (0.168 ml; 1.2 mmol) was added dropwise to a solution of 500 mg (1 mmol) of enolphosphate (III-b) and 345 mg (1.1 mmol) of thiol (IV-a) in 2 ml of N-dimethylacetamide at −15° C., and the mixture was stirred at the same temperature for 3 hours. At this time point, production of Compound (I-a) was confirmed (HPLC quantitation: 92%). The reaction solution was poured into dilute hydrochloric acid, followed by extraction with ethyl acetate. The organic layer was sequentially washed with water, a 5% aqueous sodium bicarbonate solution, and water, and dried with sodium sulfate, and a solvent was distilled off. The residue was diluted in 2 ml of ethyl acetate, 0.5 ml of benzyl alcohol and a crystal obtained in Example 2 as a seed crystal were added, and the mixture was stirred at room temperature for 2 hours. Toluene (5 ml) was slowly added, and the mixture was further stirred at room temperature for 2 hours, and cooled to 5° C. After filtration and drying, 548 mg (84%) of a benzyl alcoholated crystal of Compound (I-a) exhibiting substantially the same powder X-ray pattern as that of Example 1 was obtained.

EXAMPLE 5

[Chemical formula 14]

-continued

A benzyl alcoholated crystal (2.0 g; 3.06 mmol) of Compound (I-a) was dissolved in 12 ml of tetrahydrofuran, 1 ml of isopropanol, 3.71 ml (30.62 mmol) of N-ethylaniline, 4 ml of water, and 7.1 mg (0.2 eq) of Pd (PPh$_3$)$_4$ (Ph=phenyl) were sequentially added, and the mixture was stirred at 25° C. for 3 hours under a nitrogen stream. Then, after allowing to stand at the same temperature for 1.5 hours, and at 5° C. for 16 hours, a precipitate was filtered and dried to obtain 1.26 g (94%) of an objective material (11).

EXAMPLE 6

[Chemical formula 20]

The similar reaction to that of Example 5 was performed by reducing an amount of the Pd catalyst to be used.

Compound (I-a) (provided that an isopropyl alcoholated crystal was used) (500 mg) was dissolved in 2 ml of tetrahydrofuran (THF), 10 equivalent of N-ethylaniline, 2 ml of THF, and 1 ml of H$_2$O were sequentially added, and degassing under reduced pressure and nitrogen replacement of a charging solution were repeated three times. Further, 0.002 equivalent of Pd(PPh$_3$)$_4$ and 2 ml of THF were sequentially added, and degassing under reduced pressure and nitrogen replacement of a charging solution were further repeated three times. Under the condition of room temperature, nitrogen atmosphere and stirring with a stirrer, a reaction was performed for about 1.5 hours, and Compound (II) was initiated to be crystallized. Disappearance of raw materials, and a reaction intermediate was confirmed by HPLC, thereafter, three hours after initiation of a reaction, dimethylformamide (DMF) was added to uniformize the reaction solution. A generation rate of Compound (II) calculated from this reaction solution was 92%.

COMPARATIVE EXAMPLE 1

The reaction of Example 6 was performed using N-methylaniline in place of N-ethylaniline, and a generation rate of Compound (II) was found to be 89%. In addition, a nature of precipitated Compound (II) was viscous as compared with the case of use of N-ethylaniline, and was partially massy, and a part of the compound was adhered to a wall of a reaction vessel.

Further, the similar reaction was performed using other electron donating group-substituted anilines (e.g.: N,N-dimethylaniline, toluidine, anisidine) in place of N-ethylaniline, and a generation rate of Compound (II) was lower (yield 0 to 86%) in any case as compared with the case of use of N-ethylaniline.

COMPARATIVE EXAMPLE 2

The reaction of Example 6 was performed similarly using aniline in place of N-ethylaniline (provided that, as a solvent, THF (12V)-water (2V) was used). As shown below, when an amount of the Pd catalyst to be used was reduced, a large amount of a byproduct was generated, and a generation rate of Compound (II) was remarkably reduced.

TABLE 1

| Pd(PPh$_3$)$_4$ (eq) | Reaction time (h) | Generation rate of Compound (II) (%) |
|---|---|---|
| 0.0200 | 0.5 | 86 |
| 0.0100 | 0.5 | 84 |
| 0.0050 | 1.5 | 83 |
| 0.0025 | 5.0 | 70 |

EXAMPLE 7

[Chemical formula 21]

(1) Synthesis of 7 (Crystal of Compound (V-a))

DIAD (diethyl azodicarboxylate) (23.63 g; 1.2 eq) was added dropwise to a solution containing 26.7 g (0.1 mol, 97.1% purity) of Compound 6 synthesized by the method described in JPA (Kokai) No. 5-294970 or the above route, 26.49 g (1.35 eq) of H$_2$NSO$_2$NHBoc (Boc=t-butoxycarbonyl), and 32 g (1.22 eq) of PPh$_3$ (triphenylphosphine) in 400 ml of ethyl acetate at room temperature for 30 minutes. After stirred at the same temperature for 16 hours, ethyl acetate was distilled off under reduced pressure, and the solvent was replaced with 100 ml of toluene. A precipitated reduced entity of DIAD was filtered, and concentrated under reduced pressure. The residue was subjected to silica gel chromatography, and an elution portion at n-hexane-ethyl acetate=2:1 was concentrated to obtain 48.5 g of an objective substance 7. Crystallization from ethyl ether afforded 27.12 g (62%) of a crystal.

Mp. 115° C.

Anal for C$_{16}$H$_{27}$N$_3$O$_7$S$_2$ (FW 437.53), Calcd.; C, 43.92, H, 6.22, N, 9.60, S, 14.66, Found; C, 43.87, H, 6.20, N, 9.67, S, 14.37

$^1$H NMR (CDCl$_3$): δ 1.51 (s, 9H), 2.34 (s, 3H), 2.53-2.63 (m, 1H), 3.19-3.25 (m, 1H), 3.57-3.63 (m, 1H), 3.90-4.04 (m, 2H), 4.20-4.27 (m, 3H), 4.52-4.54 (m, 3H), 5.21-5.32 (m, 3H), 5.82-5.96 (m, 4H)

λmax$^{MEOH}$ ε(nm); 4, 310 (231)

υmax$^{Nujol}$ 3374, 3195, 1721, 1678 cm$^{-1}$

[α]$_{365}^{22°}$ +4.6±0.5°, [α]$_{436}^{22°}$ +1.2±0.4° (MeOH, C=1.001%)

Powder X-ray diffraction data is shown in FIG. 4. A peak of peak No. 23 is a peak derived from aluminum used at measurement.

(2) Synthesis of 8 from 6 (Crystal of Compound (VI-a))

DIAD (22.80 g; 1.2 eq) was added dropwise to a solution of 26.48 g (0.1 mol, 94% purity) of Compound 6, 24.89 g (1.35 eq) of H$_2$NSO$_2$NHBoc, and 29.57 g (1.2 eq) of PPh$_3$ in 244 ml of ethyl acetate at room temperature for 30 minute. After stirred at the same temperature for 16 hours, ethyl acetate was distilled off under reduced pressure, and the residue was dissolved in 260 ml of methanol. Methanesulfonic acid (3.8 ml; 1.0 eq) was added, and the mixture was stirred at 65 to 70° C. for 4 hours. After cooling, a solvent was distilled off, and the residue was added to 260 ml (2.2 eq) of a 0.5N NaOH solution, and washed with 260 ml of ethyl acetate two times. Each ethyl acetate layer was back-extracted with 234 ml (2 eq) of a 0.5N NaOH solution. The aqueous layers were combined, made acidic with hydrochloric acid, and extracted with 260 ml of ethyl acetate two times. The extracts were washed with 130 ml of water, combined, and dried with Na$_2$SO$_4$, and a solvent was concentrated under reduced pressure to obtain 6.61 g (66.1%) of a crystal of 8.

When hydrochloric acid or hydrochloric acid/methanol solution was used in place of methanesulfonic acid, the similar result was obtained.

Mp. 107-109° C.

Anal for C$_9$H$_{17}$N$_3$O$_4$S$_2$ (FW 295.38), Calcd.; C, 36.60, H, 5.80, N, 14.23, S, 21.71, Found; C, 36.58, H, 5.75, N, 14.14, S, 21.82

$^1$HNMR (CDCl$_3$): δ 1.72-1.74 (m, 2H), 2.55-2.64 (m, 1H), 3.11-3.22 (m, 1H), 3.24-3.35 (m, 2H), 3.41-3.49 (m, 1H), 4.02-4.09 (m, 2H), 4.58-4.60 (m, 2H), 4.71 (3, 2H), 5.24-5.35 (m, 2H), 5.87-6.00 (m, 2H)

$[\alpha]_D^{23°}$ −49.7±0.9° (MeOH, C=1.004%)

Powder X-ray diffraction data is shown in FIG. 3. A peak of peak No. 20 is a peak derived from aluminum used at measurement.

(3) Synthesis of 8 from 7

A 2.26N HCl/methanol solution (30.34 ml; 4 eq) was added to a solution of 7.5 g (17.14 mol) of a crystal 7 in 15 ml of methanol at room temperature, and the mixture was stirred at 40° C. for 4.5 hours. After cooling, salting out was performed by adjusting a pH at 2.5 with a 10% NaOH aqueous solution, followed by extraction with 50 ml of ethyl acetate three times. Each ethyl acetate layer was washed with 38 ml of a 6% aqueous sodium chloride solution three times. Ethyl acetate layers were combined, and dried with Na$_2$SO$_4$, a solvent was concentrated, and this was crystallized from ethyl acetate-toluene system to obtain 8 4.77 g (94.2%).

The invention claimed is:

1. A solvated crystal (provided that the solvent is benzyl alcohol optionally substituted on a ring carbon) of Compound (I-a) represented by the formula:

[Chemical formula 5]

(I-a)

wherein the content of benzyl alcohol is 1 mole equivalent relative to Compound (I-a).

2. The crystal according to claim 1, which is a benzyl alcoholated crystal.

* * * * *